United States Patent [19]

Hosang et al.

[11] Patent Number: 5,447,919
[45] Date of Patent: Sep. 5, 1995

[54] SULFATED OLIGOSACCHARIDES

[75] Inventors: Markus Hosang, Allschwil; Niggi Iberg, Basle; Thomas B. Tschopp, Ettingen, all of Switzerland; Hans P. Wessel, Heitersheim, Germany

[73] Assignee: Hoffmann-La Roche Inc., Nutley, N.J.

[21] Appl. No.: 210,115

[22] Filed: Mar. 17, 1994

Related U.S. Application Data

[63] Continuation of Ser. No. 848,577, Mar. 9, 1992, abandoned.

[30] Foreign Application Priority Data

Mar. 13, 1991 [CH] Switzerland .............................. 765/91

[51] Int. Cl.⁶ .................... A61K 31/715; C07H 11/00
[52] U.S. Cl. ........................................ 514/53; 514/54; 514/61; 536/118
[58] Field of Search ............... 536/118; 514/53, 54, 514/61

[56] References Cited

U.S. PATENT DOCUMENTS

| | | | |
|---|---|---|---|
| 4,098,995 | 7/1978 | Nair et al. | 536/118 |
| 4,359,461 | 11/1982 | Nair et al. | 536/118 |
| 4,840,940 | 6/1989 | Keine | 536/21 |
| 4,885,361 | 12/1989 | Wessel | 536/118 |

FOREIGN PATENT DOCUMENTS

| | | |
|---|---|---|
| 0230023 | 12/1986 | European Pat. Off. . |
| 2730992 | 1/1978 | Germany . |
| WO8806143 | 8/1988 | WIPO . |

*Primary Examiner*—Michael G. Wityshyn
*Assistant Examiner*—Everett White
*Attorney, Agent, or Firm*—George M. Gould; George W. Johnston; Ellen Ciambrone Coletti

[57] ABSTRACT

The use of compounds of the formula

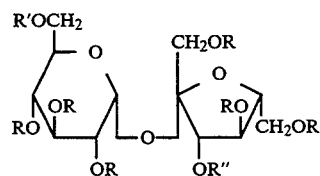

wherein R is hydrogen or a residue —SO₃M; M is a cation; and R' and R" are hydrogen or an α-glycosidically linked sulfated mono- or disaccharide residue; and at least one —SO₃M group is present per monosaccharide unit, as pharmaceutical compositions for the prevention and/or treatment of arteriosclerotic disorders and for the prevention of restenosis after invasive vascular surgery and after organ transplants.

15 Claims, No Drawings

SULFATED OLIGOSACCHARIDES

This is a continuation of application Ser. No. 07/848,577, filed Mar. 9, 1992, now abandoned.

BRIEF SUMMARY OF THE INVENTION

The present invention relates to pharmaceutical compositions for enteral or parenteral administration comprising, as active ingredients, sulfated oligosaccharides of the formula

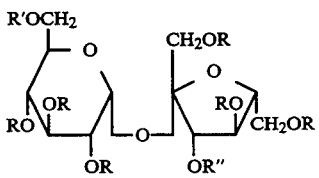

wherein R is hydrogen or a residue —$SO_3M$; M is a cation; and R' and R" are hydrogen or an α-glycosidically linked sulfated mono-or disaccharide residue;
with the proviso that at least one —$SO_3M$ group is present per monosaccharide unit.

DETAILED DESCRIPTION OF THE INVENTION

The present invention relates to pharmaceutical compositions for enteral or parenteral administration comprising, as active ingredients, sulfated oligosaccharides of the formula

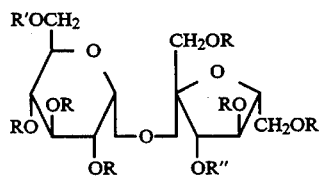

wherein R is hydrogen or a residue —$SO_3M$; M is a cation; and R' and R" are hydrogen or an α-glycosidically linked sulfated mono-or disaccharide residue;
with the proviso that at least one —$SO_3M$ group is present per monosaccharide unit.

The invention is also concerned with the use of the compounds of formula I for the treatment of arteriosclerotic disorders and for the prevention of restenosis after invasive vascular surgery and after organ transplants.

As the cation M there come into consideration all physiologically compatible cations, for example, alkali metal cations, such as, for example, $Na^+$ and $K^+$; ammonium ions and substituted ammonium ions which are derived from tertiary amines, such as, for example, triethylamine, or pyridine or imidazole; or quaternary ammonium ions, such as, for example, dodecyltrimethylammonium, ethylpyridinium and benzethonium; as well as alkaline earth metal cations, such as, for example, $Ca^{++}$. Compounds in which M is $Na^+$ are preferred.

The degree of sulfation means the number of—$SO_3M$ residues per monosaccharide unit which are present in the molecule in the preparation. For example, the degree of sulfation I therefore exists when a hexasaccharide of formula I in the preparation contains 6—$SO_3M$ residues in the molecule. The degree of sulfation in the compounds of formula I is preferably 2–3.

The compounds of formula I can be prepared by treating a corresponding tri-, tetra-, penta- or hexasaccharide with a sulfating agent and converting the reaction product into a salt or isolating it as such. Sucrose, raffinose, melezitose and stachyose are examples of such saccharides.

The sulfation of these saccharides can be carried out using known methods for the sulfation of hydroxy groups.

Examples of sulfating agents which can be used for the preparation of the compounds of formula I are $SO_3$-complexes, such as, for example, $SO_3$.pyridine, $SO_3$.trimethylamine, $SO_3$.dioxan and $SO_3$.dimethylformamide. Other examples of sulfating agents are chlorosulfonic acid, mixtures of chlorosulfonic acid and sulfuric acid; and piperidine N-sulfate.

The reaction is conveniently effected in a suitable solvent, especially a polar solvent, for example, dimethylformamide, dimethyl sulfoxide or hexamethylphosphortriamide. The reaction can be carried out at room temperature or a higher temperature, for example, at 20°–70° C., whereby the degree of sulfation can be influenced by varying the reaction duration and reaction temperature. The degree of sulfation achieved in each case can be assessed by HPLC. The working-up of the reaction mixture and, respectively, the isolation of the reaction product of formula I from the reaction mixture can be effected according to known methods, for example, by gel filtration or ultrafiltration.

The sulfated raffinose obtained from raffinose is a novel compound and as such is also an object of the invention.

The free saccharides which are used as starting materials are known or can be prepared according to known methods. Enzymatic or synthetic chemical procedures come into consideration for the preparation. The oligosaccharides can be synthesized principally using sequential synthesis or block synthesis. In this case, glycosidic bonds are formed by reacting a glycosyl acceptor with a glycosyl donor in the presence of a suitable catalyst. Derivatized glycosyl compounds which are activated at the anomeric centre, such as, for example, chlorides, bromides, fluorides, acetates, trichloro-acetimidates, alkylthio derivatives, and the like are suitable as glycosyl donors.

Those saccharide derivatives in which the OH groups to be glycosylated are free and the remaining OH groups are completely or partially protected are suitable as glycosyl acceptors. When the remaining OH groups are only partially protected the glycosylidation can be effected selectively or can be directed in a particular direction by virtue of the hydroxyl groups having a different environment.

The compounds of formula I inhibit the migration and proliferation of cells of the vascular smooth musculature and prevent proliferative arteriosclerotic lesions. Their blood coagulation-inhibiting activity is lower than that of heparin. In particular, the compounds have no in vitro anticoagulant activity, that is, they have no effect or only a very slight effect on the coagulation factors thrombin (F.IIa) and F.Xa. The compounds of formula I can therefore be used in the case of disorders which, after stimulated damage, lead to the proliferation of smooth muscle cells. In particular, the compounds can be used for the prevention of restenosis after invasive vascular surgery, endoarteriectomy, angioplasty, bypass operations with vascular transplants and synthetic vascular prosthesis as well as after organ transplants. Patients with progressive arteriosclerosis can also be treated with compounds of formula I.

The blood coagulation-ihibiting activity was determined as follows:

aPTT (activated partial thromboplastin time) Test (see Walenga et al., CRC Critical Reviews in Laboratory Sciences 22 (4) 361–389(1986)): 100 μl of citrated human plasma, which contains various concentrations of test compound, are incubated at 37° C. for 8 minutes with 100 μl of Activated Thrombofax (Ortho Diagnostics, Raritan, N.J., U.S.A.). 100 μl of prewarmed 25 mM calcium chloride solution are then added and the coagulation time is measured in a Fibrometer Coagulation Timer (Becton, Dickinson Basle).

anti-Xa Clotting Assay: 25 μl of citrated plasma having various concentrations of test compound are mixed with 75 μl of Factor Xa (Diagnostic Reagents, Thame, Oxon, Great Britain) diluted 1:100 in 0.63% citrate buffer (pH 7.3) which contains 41 mM imidazole, 82 mM NaCl and 0.1% albumin. After warming to 37° C. for 2 minutes, 200 μl of a 1:1 mixture of Factor X Deficient Plasma (Diagnostic Reagents) and Platelet Substitute (Diagnostic Reagents) are added and the mixture is incubated at 37° C. for 20 seconds. After the addition of 100 μl of pre-warmed 50 mM calcium chloride solution, the coagulation time is measured in a Fibrometer.

The activity of the test compound is given as the $IC_{50}$, which is that concentration [μg/ml] which leads to a coagulation time which is double the control value.

Inhibition of Thrombin or Factor Xa in the Chromogenic Substrate Assay (Teienet al., Thrombosis Research 10, 399–410 (1977)): The determination was effected in a Cobas-Bio centrifugal automatic spectrophotometer. The buffer solution used consisted of 50 mM Tris buffer, 180 mM NaCl, 7.5 mM EDTA $Na_2$, 1% PEG 6000 and 0.02% Tween 80, pH 8.4. The test solution consisted of 50 μl of buffer, 30μl of antithrombin III(1 U/ml), Kabi Diagnostica) and 20 μl of plasma which contained various concentrations of test compounds. 30 μl of sample solution and 20 μl of water with 180 μl of thrombin were added to the test cuvette in the automatic analyzer. After incubation at 37° C. for 240 seconds, 60 μl of S-2238 (H-D-Phe-Pip-Arg-NH.pNA, Kabi Diaguostica, Mondal, Sweden, 0.75 mM in water) and 20 μl of water were added. The liberation of pNA (p-nitroaniline) was followed during 60 seconds at 405 nm and in 10 second intervals in comparison to water as the blank. The inhibitory activity is given as the $IC_{50}$, which is the concentration [μg/ml] at which the amidolytic activity of thrombin is reduced by 50% in comparison to the plasma control value.

The inhibition of Factor Xa was measured in the same manner using a solution of Factor Xa (2.8 nkat/ml and 2 nM S-2222 (Bz-CO-Ile-Glu-Arg-NH.pNA, Kabi Diagnostica) in water in place of thrombin and, respectively, S-2238.

The anti-proliferative activity of the substances was determined in cell cultures as follows: smooth muscle cells of rats (cultivated in DMEM with 10% FCS at 37° C. and 5% $CO_2$) were applied to cell culture plates with a density of $8 \times 10^3$ cells/well. After 4 hours, the number of adhered cells was determined and the substances to be tested (100 mg/ml) were added. Cells to which test substance was not added served as a comparison and heparin (100 mg/ml) served as a positive control. The cells were incubated for 7 days and then the cell number was determined. The antiproliferative activity of the individual substances was calculated as the % inhibition in comparison to non-inhibited growth:

$$\% \text{ Inhibition} = \frac{\text{cell number}_{(-)} - \text{cell number}_{(inhib)}}{\text{cell number}_{(-)} - \text{cell number}_{(d=0)}} * 100$$

wherein cell number$_{(d=0)}$=cell number after 4 h
cell number$_{(-)}$=cell number to which test substances was not added, after 7 days.
cell number $_{(inhib)}$=cell number with 100 μl/ml of the test substance The results obtained in the experimental procedures described above with compounds of formula I are listed in Table 1. Heparin served as the reference compound.

TABLE 1

| Compound of Example | Anti-proliferative activity % inhibition | Anti-coagulation activity $IC_{50}$ [μg/ml] | | | |
|---|---|---|---|---|---|
| | | Coagulation inhibition aPTT | Amidolytic activity | | |
| | | | Xa | Thrombin | F.Xa |
| 1 | 41 | 27 | >1000 | >1000 | >1000 |
| 2 | 25 | 150 | 250 | >1000 | >1000 |
| 3 | 49 | 11 | 32 | >1000 | >1000 |
| Heparin | 47 | 1.2 | 0.6 | 1.9 | 2.7 |

The test results show that the compounds in accordance with the invention have an anti-proliferative activity which, in contrast to the likewise anti-proliferatively active heparin, is not accompanied by or is accompanied, to a very insignificant extent, by an anticoagnlant activity.

The medicaments based on the compounds in accordance with the invention can be administered enterally, for example, orally in the form of tablets, coated tablets, dragées, hard and soft gelatin capsules, solutions, emulsions or suspensions, or rectally, for example, in the form of suppositories. However, the administration is preferably effected parenterally, for example, in the form of injection solutions.

For the manufacture of tablets, coated tablets, dragées and hard gelatin capsules, the active ingredient can be mixed with z5 pharmaceutically inert, inorganic or organic excipients. As such excipients for tablets, dragées and hard gelatin capsules there can be used, for example, lactose, maize starch or derivatives thereof, talc, stearic acid or its salts. Suitable excipients for soft gelatin capsules are, for example, vegetable oils, waxes, fats, semi-solid and liquid polyols; depending on the nature of the active ingredient no excipients are, however, usually required in the case of soft gelatin capsules. Suitable excipients for the manufacture of solutions and syrups are, for example, water, polyols, saccharose, invert sugar and glucose. Suitable excipients for injection solutions are, for example, water, alcohols, polyols, glycerine and vegetable oils. Suitable excipients for suppositories are, for example, natural or hardened oils, waxes, fats and semi-liquid or liquid polyols.

The pharmaceutical preparations can contain, in addition, preservatives, solubilizers, stabilizers, wetting agents, emulsifiers, sweeteners, colorants, flavorants, salts for varying the osmotic pressure, buffers, coating agents or antioxidants. In the case of enteral administration, the resorption of the active ingredient can be increased with the aid of liposomes.

The dosage of the active ingredient can vary within wide limits and will, of course, be fitted to the individual requirements in each particular case. In general, in the case of parenteral administration, a dosage of about 0.1 to 100 mg/kg, preferrably of about 1.5 to 15 mg/kg, per day should be appropriate for adults, although the upper limit just given can also be exceeded when this is shown to be indicated.

EXAMPLE 1

A solution of 2.0 g of D-raffinose pentahydrate in 50 ml of absolute dimethylformamide was stirred at 60° C. for 20 hours in the presence of 10.3 g of sulphur trioxide-trimethylamine complex, whereby a precipitate separated. The solvent was decanted off. The residue was washed with methanol, dissolved in 64 ml of aqueous 10% sodium acetate solution and concentrated. The residue was taken up several times in water and evaporated to remove trimethylamine. The residue was gel-chromatographed (Sephadex® LH 20) in order to remove salts. After freeze-drying there were obtained 5.28 g of sulfated raffinose, S=19.89%, AS (average degree of sulfation) about 2.8.

EXAMPLE 2

A solution of 2.0 g of D-melezitose monohydrate in 50 ml of absolute dimethylformamide was stirred at 60° C. for 18 hours in the presence of 11.7 g of sulphur trioxide-trimethylamine complex, whereby a precipitate separated. Working-up as in Example 1 gave, after the addition of 69.1 ml of 10% aqueous sodium acetate solution and removal of salts, 5.0 g of sulfated melezitese, S=20.0%, AS about 3.0.

EXAMPLE 3

A solution of 850 mg of stachyose tetrahydrate in 20 ml of absolute dimethylformamide was stirred at 50° C. for 24 hours in the presence of 4.5 g of sulphur trioxide-trimethylamine complex, whereby an oily precipitation resulted. Working-up as in Example 1 gave, after the addition of 22 ml of 10% aqueous sodium acetate solution and removal of salts, 2.0 g of sulfated stachyose, S=19.5%, AS about 2.8.

EXAMPLE 4

| Tablets: | | |
|---|---|---|
| 1 | Compound of formula I | 500 mg |
| 2 | Lactose, anhydrous | 150 mg |
| 3 | Microcrystalline cellulose | 150 mg |
| 4 | Polyvinylpyrrolidone | 40 mg |
| 5 | Talc | 50 mg |
| 6 | Magnesium stearate | 10 mg |
| | Tablet weight | 900 mg |

Ingredients 1–4 are sieved and mixed. This mixture is granulated with demineralized water and the dried granulate is mixed with ingredients 5 and 6. The mixture is pressed to tablets of suitable form.

EXAMPLE 5

| Pellets: | | |
|---|---|---|
| 1 | Compound of formula I | 500 mg |
| 2 | Microcrystalline cellulose | 200 mg |
| 3 | PRIMOGEL | 70 mg |
| 4 | Flavor powder | 10 mg |
| 5 | Talc | 20 mg |

Mixed and sieved ingredients 1–3 are moistened sufficiently with demineralized water and pressed through a suitable perforated disk using an extruder. The extrudate is transferred to a pelleting plate, rounded off to beadlets and subsequently dried. They are then treated with sieved ingredients 4 and 5 and filled into paper sachets (or similar).

EXAMPLE 6

Injection solution:

In order to produce an injection solution, 50 mg of a compound of formula I and 0.5 mg of Tris buffer are dissolved in water for injection ad 1 ml and the pH value is adjusted to 7.4. The solution is filtered sterile and, after filling into ampoules, is autoclaved.

We claim:

1. A method for the treatment of arteriosclerotic disorders comprising administering to a host in need of such treatment an effective amount of a compound of the formula

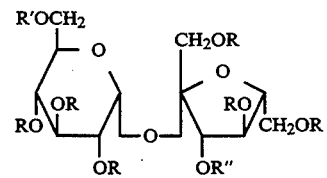

wherein R is hydrogen or a residue —SO$_3$M; M is a cation; and R' and R" are hydrogen or an α-glycosidically linked sulfated mono- or disaccharide residue; and at least one —SO$_3$M group is present per monosaccharide unit.

2. The method of claim 1, wherein the compound of formula I is a sulfated tri- or tetrasaccharide.

3. The method of claim 2, wherein the compound of formula I is sulfated raffinose.

4. The method of claim 2, wherein the compound of formula I is sulfated melezitose.

5. The method of claim 1, wherein the degree of sulfation of the compound of formula I is 2–3.

6. A method for the prevention of restenosis after invasive vascular surgery and after organ transplants comprising administering to a host in need of such treatment an effective amount of a compound of the formula

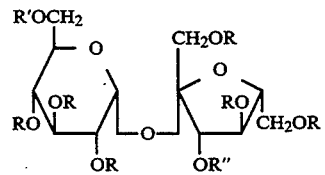

wherein R is hydrogen or a residue —SO$_3$M; M is a cation; and R' and R" are hydrogen or an α-glycosidically linked sulfated mono- or disaccharide residue; and at least one —SO$_3$M group is present per monosaccharide unit.

7. The method of claim 6, wherein the compound of formula I is a sulfated tri- or tetra saccharide.

8. The method of claim 6, wherein the compound of formula I is sulfated raffinose.

9. The method of claim 6, wherein the compound of formula I is sulfated melezitose.

10. The method of claim 6, wherein the degree of sulfation of the compound of formula I is 2–3.

11. A pharmaceutical composition for enteral or parenteral administration in the prevention of restenosis after invasive vascular surgery and after organ transplants comprising a compound of the formula

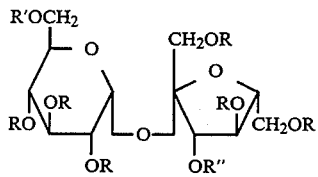

wherein R is hydrogen or a residue —SO$_3$M; M is a cation; and R' and R" are hydrogen or an α-glycosidically linked sulfated mono- or disaccharide residue; and at least one —SO$_3$M group is present per monosaccharide unit and a pharmaceutically conventional carrier.

12. The pharmaceutical composition of claim 11, wherein the compound of formula I is a sulfated tri- or tetrasaccharide.

13. The pharmaceutical composition of claim 11, wherein the compound of formula I is a sulfated raffinose.

14. The pharmaceutical composition of claim 11, wherein the compound of formula I is a sulfated melezitose.

15. The pharmaceutical composition of claim 11, wherein the degree of sulfation of the compound of formula I is 2–3.

* * * * *